US006738662B1

United States Patent
Frank

(10) Patent No.: US 6,738,662 B1
(45) Date of Patent: May 18, 2004

(54) ELECTROLYTIC SUBSTANCE INFUSION DEVICE

(76) Inventor: Steven R. Frank, 11192 Twin Spruce Rd., Golden, CO (US) 80403

( * ) Notice: Subject to any disclaimer, the term of this patent is extended or adjusted under 35 U.S.C. 154(b) by 57 days.

(21) Appl. No.: 09/718,521

(22) Filed: Nov. 21, 2000

Related U.S. Application Data

(63) Continuation of application No. 09/182,581, filed on Oct. 29, 2001, now abandoned.

(51) Int. Cl.[7] .................................................. A61N 1/30
(52) U.S. Cl. ........................ 604/20; 604/890.1; 604/501
(58) Field of Search ........................ 604/20, 19, 890.1, 604/892.1, 500, 501; 361/768

(56) References Cited

U.S. PATENT DOCUMENTS

| | | |
|---|---|---|
| 3,831,598 A | 8/1974 | Tice |
| 3,918,459 A | 11/1975 | Horn |
| 3,964,477 A | 6/1976 | Ellis et al. |
| 4,305,390 A | 12/1981 | Swartz |
| 4,411,648 A | 10/1983 | Davis et al. |
| 4,474,570 A | 10/1984 | Ariura et al. |
| 4,774,833 A | 10/1988 | Weibler et al. |
| 4,808,152 A * | 2/1989 | Sibalis .......................... 29/825 |
| 4,821,700 A | 4/1989 | Weibler et al. |
| 5,254,081 A * | 10/1993 | Maurer et al. ................. 604/20 |
| 5,306,287 A | 4/1994 | Becker |
| 5,322,520 A | 6/1994 | Milder |
| 5,328,451 A | 7/1994 | Davis et al. |
| 5,498,248 A | 3/1996 | Milder |
| 5,571,149 A | 11/1996 | Liss et al. |
| 5,676,648 A | 10/1997 | Henley |
| 5,749,845 A | 5/1998 | Hildebrand et al. |
| 5,805,423 A * | 9/1998 | Wever et al. ................ 361/760 |
| 5,846,217 A | 12/1998 | Beck et al. |
| 5,865,787 A | 2/1999 | Shapland et al. |
| 6,001,088 A | 12/1999 | Roberts et al. |
| 6,175,763 B1 * | 1/2001 | Sorenson et al. .............. 604/20 |

* cited by examiner

*Primary Examiner*—Brian L. Casler
*Assistant Examiner*—Jeremy Thissell
(74) *Attorney, Agent, or Firm*—Welsh & Flaxman LLC

(57) ABSTRACT

A portable, self-contained hand-held device for treating an illness or infection of tissue of a body is provided. The device comprises an integrally mounted metal ion source contactable with the tissue with an antimicrobial substance on at least a portion of the metal ion source. A conducting surface is contactable with the user. An automatically controlled and modulated field electrically is connected to the metal ion source and the conducting surface with the control system creating an electric field between the metal ion source and the conducting surface through the body wherein the antimicrobial substance is ionized upon application of the electric field thereby profusing the substance into the infected tissue. In another embodiment, a bandage is provided for adhering to the skin of the user.

21 Claims, 3 Drawing Sheets

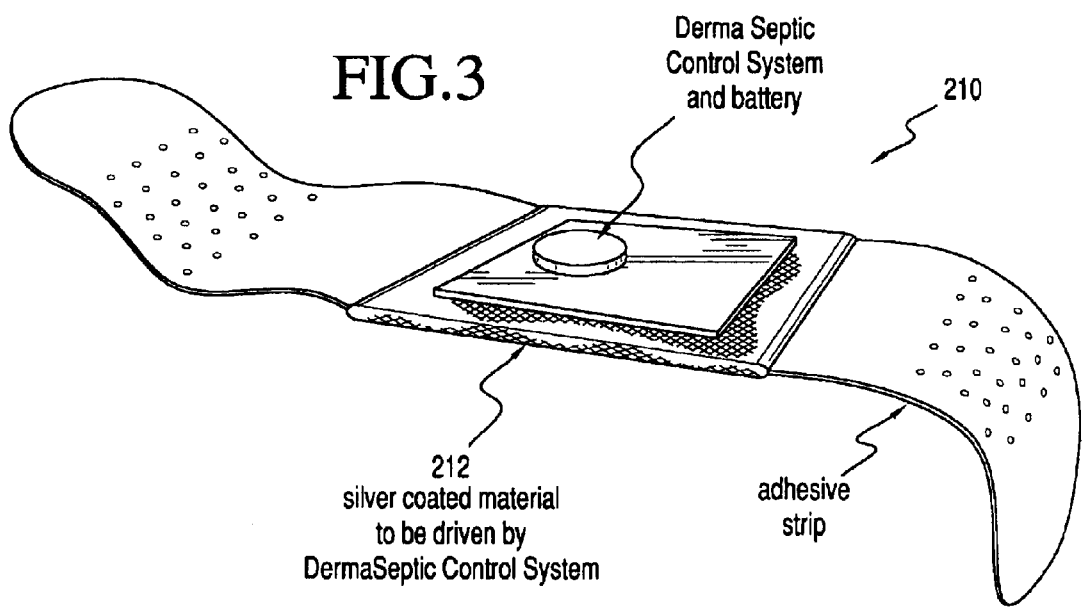
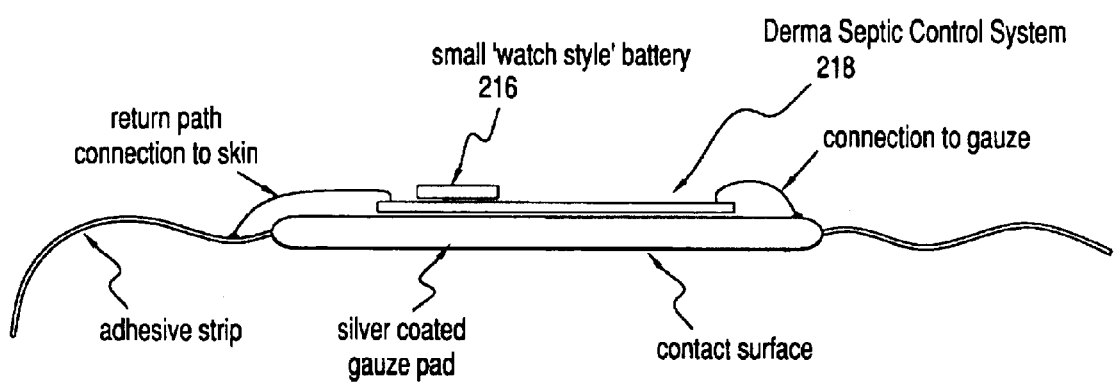

ELECTROLYTIC SUBSTANCE INFUSION DEVICE

The present application is a continuation of patent application Ser. No. 09/182,581, filed on Oct. 29, 1998, entitled "Electrolytic Substance Infusion Device" now abondoned.

BACKGROUND OF THE INVENTION

1. Field of the Invention

This invention relates generally to a treatment device for application to body tissue for treatment of injuries and illnesses and, more particularly, it relates to a treatment device which electrolytically infuses a substance into the body tissue upon application of an electric field by the device thereby providing an enhanced and synergistic antimicrobial benefit or improvement to the injury or illness.

2. Description of the Prior Art

Many microorganisms including, but not limited to, virus, bacteria, fungus, etc., exist in the human body. It has been estimated that approximately one-third (⅓) of the United States population harbors pathogenic microorganisms such as several species and strains belonging to the Herpes Simplex family of viruses. The Herpes Simplex family of viruses is responsible for such disease outbreak states as "Cold Sores". These lesions are often instigated by a systemic malady such as a cold or flu. The lesions can also be provoked by sunlight, emotional stress, and are aggravated by various food substances including caffeine and chocolate.

When an outbreak occurs, the outbreaks occur most frequently around the mouth area and produce large, unsightly, painful sores. During the time that the sore is exposed, the condition is highly contagious and the virus is transmitted readily through both direct contact and indirect contact. Furthermore, the lesions take one (1) to two (2) weeks to heal and occur with a frequency of every few months to every few years, depending on the individual.

To date, there is no known cure for the "Cold Sores" malady. The pathogenic microorganisms that cause the malady, such as Herpes Simplex virus, lay dormant, hiding from the body's natural immune system in the nerve cells until an outbreak occurs. Several therapies have been explored which range from topical antibiotic salves to intravenously administered systemic doses of antibiotics. These therapies have demonstrated only limited success at reducing the duration and severity of a "Cold-Sore" outbreak.

Concerning the treatment of warts, it has been noted that a virus, which lives in the root of the wart, causes warts. The site where the virus lives can actually be one (1 mm) millimeter to two (2 mm) millimeters below the surface of the surrounding tissue. Unfortunately, simply removing or dissolving the tumorous protrusion above the root does not remove the remaining root which still harbors the virus. With conventional treatment methods, eventually, the wart will return.

In the past, iontophoresis machines were constructed to treat warts and other viruses. These machines are very large to treat large areas of tissue and have been nonportable due to their size and required skilled operation by a trained practitioner to achieve the appropriate dose and rate. The conventional iontophoresis machines also required constant monitoring to maintain the desired rate during the procedure.

The conventional iontophoresis machines focus on delivering molecular compounds (drugs) to subcutaneous regions of infected tissue. The drugs are immunomodulators, which cause the T-cells, and K-cells to more actively attack an infection. Some infections like Herpes and warts, hide inside cells during their progeny producing (multiplying) phase and are therefore as resistant to profused antiviral drugs as to the systemically or topically administered versions.

Still other seeming predicate devices give the illusion of antimicrobial action by simply denaturing normal viable cells in the treated region. These devices are less effective and typically render tissue damage due to the medications or the generated free radicals. This tissue damage caused by excessive current density or in some cases the iontophoresis delivery of antiviral drugs, is actually counter productive to the therapy as a whole. A number of virus (particularly the ones producing warts) will remain largely dormant within host cells until the host cell begins to die. This impending death of the host cell triggers the virus to produce progeny, which go on to infect adjacent cells. Thus by killing the host cell, one actually causes the infection to broaden.

Some of the existing systems are so complex or cumbersome as to render them un-useable for anything other than laboratory work. Some previous techniques to fight Herpes required control areas flooded with Methylene Blue and then exposed to a certain wavelength of light. This is only practical in a laboratory environment and is far too sophisticated and expensive for general use. Still other previous systems required large bench-top units which had to be operated by trained personnel and some utilized control pharmaceutical substances which are costly and showed insufficient efficacy to warrant commercialization. Furthermore, pre-existing silver iontophoresis devices offer no or limited control over the dose, rate and penetration.

Therefore, a need exists for a device, which provides an effective treatment for warts by treating the root of the wart through the wart's tumorous protrusion. Additionally, there exists a need for a device, which provides an electrolytic substance infusion device for treating cold sores and other lesions. Furthermore, a need exists for a device, which treats any tissue-based viral, bacterial, or fungal infection through electrolytic substance infusion.

SUMMARY

The present invention is a device for treating an illness or injury of tissue of a body. The device comprises at least a first electrode contactable with the tissue and at least a second electrode contactable with the tissue. A control system is electrically connected to the first electrode and the second electrode with the control system creating an electric field between the first electrode and the second electrode through the body. Silver, acting as an antimicrobial substance is on or comprised of at least a portion of the first electrode with the substance being ionized upon application of the electric field thereby profusing the ionic silver into the tissue.

In another embodiment of the present invention, the substance is selected from the group consisting of any ionic substance including, but not limited to, zinc, copper and silver. Furthermore, preferably, the device treats maladies selected from the group consisting of Herpes-type outbreaks, colds-type maladies, skin cancers, sub-dermal tumors, warts, acne, cold sores, and germicidal or dermatological infections.

The device further comprises an indicator signal for indicating activation of the control system and indication that a satisfactory does is/has been delivered. Furthermore, preferably, the device further comprises an embedded microcontroller or other circuitry for controlling the delivery rate, application waveform and the dose of the silver ions.

In yet another embodiment of the present invention, the device further comprises a small compact housing with the power source positioned within the housing and the first and second electrodes being mounted on the housing.

In another embodiment of the present invention, the microcontroller is activated upon the first and second electrodes contacting the skin. The applied field or waveform is then generated by the embedded microcontroller from the low-voltage battery contained within the box. The microcontroller directly controls the dc/dc switching converter to maintain the desired voltage to produce the optimal infusion rate and waveform.

This completely self-contained auto-turn-on device makes highly effective silver iontophoresis for the treatment of dermatological infections both very portable and very inexpensive.

BRIEF DESCRIPTION OF THE DRAWINGS

FIG. 3 is a perspective view illustrating a bandage device of the electrolytic substance infusion device, constructed in accordance with the present invention, for treating external skin maladies;

FIG. 4 is a sectional side view illustrating the bandage device of the electrolytic substance infusion device of FIG. 3, constructed in accordance with the present invention.

DETAILED DESCRIPTION OF THE PREFERRED EMBODIMENTS

Figure 1:
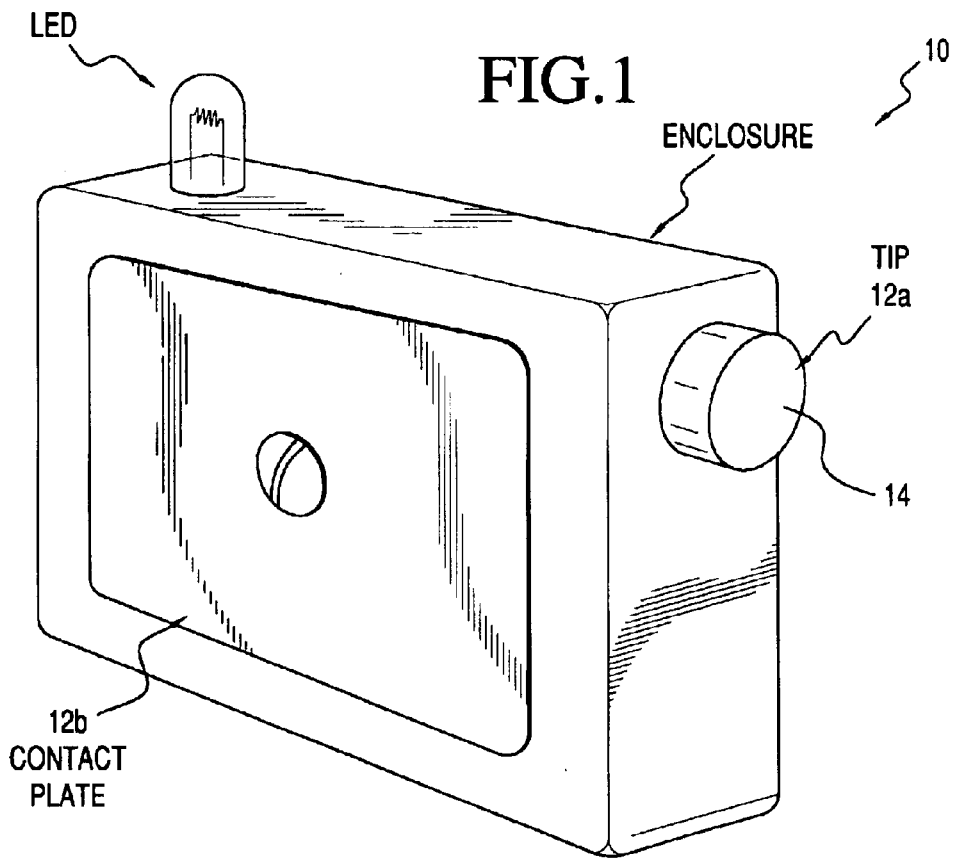
FIG. 1 is a perspective view illustrating a hand-held device embodiment of the electrolytic substance infusion device, constructed in accordance with the present invention, for treating external skin maladies.

As illustrated in FIG. 1, the present invention is an electrolytic substance infusion device, indicated generally at 10. The infusion device 10 has at least two electrodes 12 having a surface 14. The electrodes 12 are electrically connected to the infusion device 10.

Figure 2:
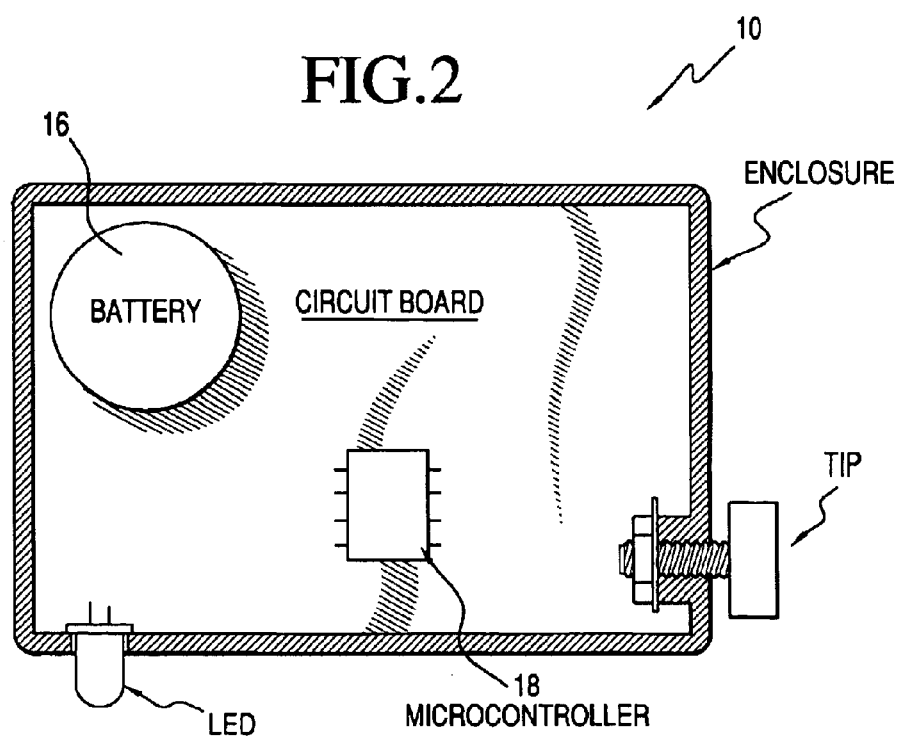
FIG. 2 is a sectional side view illustrating the hand-held device embodiment of the electrolytic substance infusion device of FIG. 1, constructed in accordance with the present invention.

As illustrated in FIG. 2, the infusion device 10 further has a power source 16 including, but not limited to, a battery, for powering a microcontroller or control system 18, which generates and applies the electric field between the electrodes 12. The treatment electrode 12a, is comprised of a substance to be administered in an ionic form, or administered in a form that can be either disassociated, mobilized, or affected by means of the small electric field. Examples of the substance covering include, but are not limited to, Zinc, Copper, Silver, etc., since these substances have noted antimicrobial properties. With the substance comprising the surface 14 of the electrode 12a, the infusion device 10 of the present invention provides an enhanced and synergistic antimicrobial benefit or improvement by killing or otherwise eliminating microorganisms including, but not limited to, virus, bacteria, fungus, etc. It should be noted that the electrode 12a can be constructed from the antimicrobial substance, coated with the antimicrobial substance, and/or used to profuse the antimicrobial substance.

As noted in FIGS. 1 and 2, the device does not include wires. A circuit board 17 having a microcontroller 18 which controls the electric field between the metal ion source 12a and conducting surface 12b is shown. Circuit board 17 also functions to connect the metal ion source 12a to the conducting surface 12b and microcontroller 18 without the use of wires. A screw 15 not only holds the conducting surface 12b to the housing or enclosure 13, but it also enters the circuit board 17 just as threaded end 12c of metal ion source 12a enters the circuit board. Thus, upon user contacting of the metal ion source 12a and the conducting surface 12b completes the circuit and the electric field causes the metal ion source 12a to be ionized and perfuse metal ions into the user's tissue and the visual indicator 19 to light. The visual indicator 19 is also directly connected to the circuit board 17.

Figure 5:
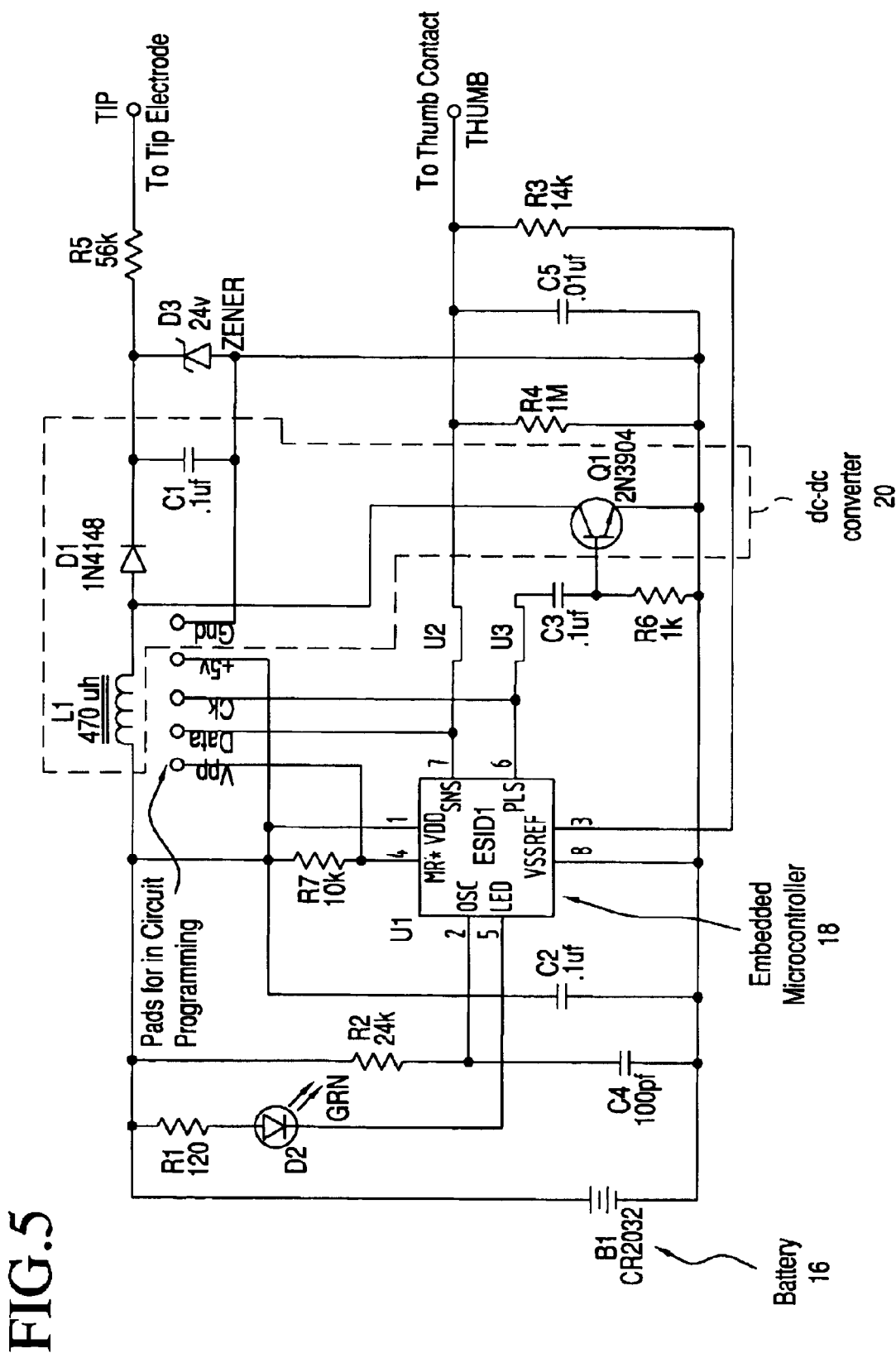
FIG. 5 is a schematic view illustrating the circuitry of the electrolytic substance infusion device, constructed in accordance with the present invention.

As illustrated in FIG. 5, the infusion device 10 of the present invention contains the small power source 16 including, but not limited to, a battery, which when powering the embedded microcontroller 18 to produce the appropriate driving waveform or voltage through the control of the DC/DC converter 20 and applied to the electrodes 12 causes an electric field to be carried through the tissue that is to be treated. The electric field can be any waveform that is advantageous to a particular therapy and can be unipolar or bipolar. An alternating field would serve to move ions from all electrodes 12. The unipolar field would deliver the substance preferentially from a particular electrode 12 and would drive the substance deeper into the tissue for therapies where subdermal interaction is required. The bipolar field would tend to leave the substance nearer to the skin surface for therapies that warrant a more external application.

Currently, time-release medication patches rely upon diffusion to carry the drug or therapeutic agent into a region producing a natural gradient and requiring high doses at the point of administration in order to deliver acceptable levels at a distance from the contact point. There can also be natural barriers to the diffusion as different tissues can sweep away the substance or block its flow entirely. There is no other effective means for delivering ionic silver subdermally.

With the infusion device 10 of the present invention, when the substance is profused electrolytically and the electrodes 12 are in reasonably close proximity, the electric field mobilizes, drives, or drags the substance through a region to the exit electrode 12. The electric field also tends to focus the flow of substance and allow a more even distribution as the depth into the tissue increases.

Experimentation by the Applicant of the present application has shown that using an electrode 12 which is comprised of or coated with a silver compound in contact with a lesion, will profuse sufficient ionic silver into a region of tissue to attenuate the viral or bacterial load far more effectively than anti-viral or anti-biotic salves. The infusion device 10 constructed by the inventor using his technique have caused complete remission of HSV lesions, warts, and acne in remarkably short order, e.g., three (3) to five (5) times faster than conventional means. Additionally, infected cuts and scrapes have been rendered infection-free and healing was notably improved.

One of the advantages of using the infusion device 10 of the present invention for treating dermatological infections is that unlike salves, the germicidal effects are profused into the tissue where they remain active and effective for twelve (12) to twenty-four (24) hours. With a salve, the bulk of the agent remains on the surface of the skin and can be easily washed or wiped away during normal daily activities. Additionally, the carrier for the active agent in salves tends to block air access to the tissue prolonging the scabbing and healing process.

VARIOUS PREFERRED EMBODIMENTS OF THE PRESENT INVENTION

The Hand-held Device:

As illustrated in FIGS. 1 and 2, the infusion device 10 of the present invention includes a hand-held device 110 providing either an attached electrode 112, or a free electrodes 112, positionable and easily moveable about an area to be treated. The electric field is applied and controlled directly by the hand-held device 110. In this manner, the electrodes 112 are coated with a conductive media, such as a hydrogel, and then are moved about a tissue area to cause the dispersion of a substance into a region, which could not be easily covered with a bandage device.

In one specific embodiment of the hand-held device 110, as illustrated in FIG. 6, the treating electrode 112a is composed of a silver compound and a conductive contact 112b is provided to complete the circuit. The user simply makes contact to the conductive contact 112b with a thumb and holds the treating electrode 112a to the area to be treated. The hand-held device 110 then provides a controlled field in order to produce the appropriate dose, rate, and penetration at the electrode 112a causing the profusion of the ionic material into the lesion or wound. The hand-held device 110 can be used as a general-purpose germicide treating everything from cuts and scrapes to cold sores, canker sores, warts, and any other dermatological condition, which requires a germicide.

The All Purpose Bandage:

As illustrated in FIG. 2, the infusion device 10 of the present invention is a bandage-shaped device 210 containing a small power source 216, such as a disposable battery or the like. In this embodiment, the infusion device 10 has a main contacting electrode 212a comprised of a silver mesh embedded within the bandage device 210 with the return electrode 212b contacting the tissue on one side of the wound of the user. The bandage device 210 could be constructed in various shapes and sizes and could be made in varying porosities to permit a desired amount of air to reach the surface of the lesion. The substance administered into the wound could be silver ions or any other antimicrobial agent. The term "antimicrobial agent" means anti-viral, anti-fungal, and anti-bacterial. The power source 216 within the bandage device 210 could be activated prior to use by simply stretching the bandage device 210. The stretching of the bandage device 110 ruptures the thin polymer sac internal to the power source 216, which contains the electrolyte for the battery cell. The power source 216 would then become active and provide charge movement for some predetermined period of time based on the design of the bandage device 210. Alternatively, the control system 218 would sense patient connection as shown in the example schematic when the bandage device 210 is applied, thereby allowing use of a simple battery 216 and inhibiting current flow to the control system 218 and electrodes 212 until the bandage device 210 is applied to the wound.

In the present embodiment, instead of the power source 216 being a battery, the power source 216 could include a capacitor. The capacitor is charged prior to use with a simple charging device containing a battery or other source of power. In the case of a one-hundred (100) microamps current flow, a capacitor of 0.01 Farads provides sufficient current flow for ten (10) minutes when charged to a few volts. Each one hundred (100) microamps-second could, for example, electrolytically profuse approximately $6 \times 10^{14}$ molecules into the tissue. In the case of silver, each microamps-second profuse approximately $1 \times 10^{-7}$ grams of silver ions into the tissue sufficient to treat tissue to a depth of several milliliters.

The generation of the waveforms of the infusion device 10 of the present invention can be controlled by the small microprocessor 18, such as a PIC12C5XX, requiring less than fifteen (15) microamps to operate. The microprocessor 18 can be procured in die form with dimensions of approximately 0.1 inch×approximately 0.1 inch and for a very low expense, the microprocessor 18 can easily be incorporated into the bandage, patch, or other delivery system as the entire control system can be made smaller than ¼ square inch. With the microprocessor 18 of the infusion device 10, the actual field strength can be monitored and integrated to allow the delivery of precise amounts of ionic substance at precise rates even though the ohmic contact to the region of interest will vary dramatically.

It should be noted that with the infusion device 10 of the present invention, the actual dose must be correct over a wide range of different tissue impedances. For example, if too much silver is delivered to a region, a brown discoloration will.occur on the skin that generally requires a couple of days to dissipate. If too little silver is delivered to a region, the antimicrobial effect of the silver will not be sufficient to treat the injury or illness. Alternatively, preferably, the electric field can be controlled by use of a constant current source, which is controlled by a fixed component value or profiled and modified by the microcontroller 18 previously described.

The infusion device 10 of the present invention goes beyond the present state of the art to actually deliver ionic silver subdermally, through an electrolytic means to the treatable region of interest. It generates the applied waveform directly from the embedded microcontroller 18 operated dc—dc converter allowing the use of very low voltage power sources such as a common coin type lithium battery. The present invention applies the appropriate dose and rate without any user control. All that is required is for the user to touch it to the treatment site. In doing so, the infusion device 10 inhibits microorganism growth in the specific region of interest thereby inhibiting the need for systemic doses of antibiotics, in many cases. The infusion device 10 of the present invention provides a better and more effective means of treatment for complicated tissues such as "Cold Sore" lesions and tissues that are poorly served by the capillary structure. The required micrograms of substance per milliliter of tissue can be achieved to the depths require to reach the colonies without relying on diffusion and capillary action. The total body-burden of the active agent can be one-hundred (100) to one thousand (1000) times less than what would be expected for systemically administered antibiotics or anti-virals since the dose will be administered directly to the site.

The infusion device 10 of the present invention also allows the construction of bandages, which allow more open-air contact and facilitate rapid skin regeneration in existing wounds or lesions.

Since the infusion device 10 of the present invention causes the profusion of antimicrobial substances through the healthy tissue into a region that is defined by the electrode configuration, the infusion device allows the beneficial effects of the substance to reach an area far greater than that of a simple impregnated device. A simple impregnated conventional device tends by its very nature to only protect the region immediately surrounding the boundary of the device and the tissue. Additionally, a device that is impregnated with an antimicrobial agent tends to hold onto the agent quite well and this renders the germicide far less effective as the virus or bacteria has limited exposure to it. The infusion device 10 of the present invention, on the other hand, provides the smallest possible particles of the agent in an ionic form, which cause it to be readily bound to the germ causing more effective germicidal effects.

Although there are currently available topical salves, which contain antimicrobial substance, the salves rely upon diffusion to reach subcutaneous regions and thus do so rather poorly. The salves tend to be applied so heavily in order to have any effect, that they discolor and kill healthy skin cells. The technique of the present invention of electrolytically profusing substances into the tissue has the significant advantage of requiring far fewer molecules of a substance to achieve the same or higher level of results. Additionally, since the substance is deposited subcutaneously, there is no concern about the amount that is lost to unintended mechanical removal from the surface while the subject is waiting for penetration.

The devices and therapies described herein could be used to combat a range of lesions from cold sores to warts. The infusion device 10 is a completely self-contained totally automatic means for treating infections and cold sores. Unlike conventional devices, the infusion device 10 of the present invention can be produced for low costs and occupies less than a cubic inch. Using the infusion device 10 requires no skill to be used correctly. Its very activation is automatic upon contact with the user's skin.

Also unlike conventional devices, the applied field waveform is dynamically and automatically controlled to optimize the administration of the ionic silver to depths where it can effectively dispatch the colonizing bacteria and proliferating virus. The silver-ion administration that is utilized in the present invention overcomes these shortcomings by acting directly on inhibiting the virus without requiring the support of the immune system in order to inactivate or destroy. Additionally, due to the single atom ionic nature of the present invention, the anti-microbial silver ions pass through the cell walls of the infected tissue destroying the virus while they remain hidden.

The infusion device 10 utilizes silver ions, which move freely across the peptidechain cell walls and disable the virus without killing the host thereby far more effectively terminating an infection or a viral outbreak. The infusion device 10 offers this control automatically via a preprogrammed response to the dynamically changing tissue impedance and waveform control to facilitate penetration. By controlling the dose rate and dose automatically as the tissue impedance changes, no user insight or understanding is required. The ability to produce the necessary voltages and waveforms from small and inexpensive batteries within a compact, inexpensive and rugged device places this novel and effective therapy in the hands of the general population. Rendering this terrific germicidal activity simply and cost effectively without the use of drugs, obviates the need for professional supervision and brings this therapy to a population of far greater number than predicate devices which are all focused on transdermal drug delivery. By directly generating the applied voltage under microcontroller control, the infusion device 10 offers far more efficient battery use prolonging system life. Additionally, this control allows more flexibility in the applied waveforms.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements, which are disclosed herein.

What is claimed is:

1. A portable hand-held device for treating an illness or infection of tissue of a body, the device comprising:

a housing;

a metal ion source mounted on the exterior of the housing which is directly contactable with the tissue;

a conducting surface mounted on the exterior of the housing which is contactable with the user; an automatically controlled and modulated field electrically connected to the metal ion source and the conducting surface automatically activated upon the metal ion source contacting the tissue and the conducting surface contacting the user;

wherein an electric field is created between the metal ion source and the conducting surface through the body such that the electric field causes the metal ion source to be ionized and perfuse metal ions into the tissue.

2. The device of claim 1 wherein the metal ion source is selected from a group of ionizable materials including zinc, copper and silver.

3. The device of claim 1 further comprising an indicator signal for indicating activation of the electric field and correct delivery of a selected dose and dose rate.

4. The device of claim 1 wherein the device treats maladies selected from the group consisting of Herpes-type outbreaks, warts, acne, cold sores, and germicidal on dermatological infections.

5. The device of claim 1 further comprising circuitry for controlling the delivery rate of the metal ions, dose of the metal ions, waveform, and voltage.

6. The device of claim 1 further comprising a power source positioned within the housing and a control system mounted within the housing which automatically controls and modulates the electric field.

7. The device of claim 6 wherein the control system includes a controllable DC-to-DC converter to generate the required voltages and waveforms from a single cell battery to operate the device.

8. The device of claim 1 wherein the electric field is a bipolar field at low frequencies for maintaining a surface only distribution of the metal ions.

9. The device of claim 1 further comprising a microcontroller which controls the electric field between the metal ion source and conducting surface and a circuit board which connects the metal ion source to the conducting surface and microcontroller without the use of wires.

10. A completely self-contained disposable bandage device for treating an illness or infection of tissue of a body, the bandage device comprising:

an adhesive strip;

a metal ion source mounted on the adhesive strip which is directly contactable with the tissue when the adhesive strip is secured to a user;

a conducting surface mounted on the adhesive strip which is contactable with the user when the adhesive strip is secured to the user;

an automatically controlled and modulated field electrically generating system attached to the adhesive strip and connected to the metal ion source and the conducting surface which is automatically activated upon the metal ion source contacting the tissue and the conducting surface contacting the user skin proximate the tissue;

wherein an electric field is created between the metal ion source and the conducting surface through the body such that the electric field causes the metal ion source to be ionized and perfuse metal ions into the tissue.

11. The device of claim 10 wherein the metal ion source is selected from a group consisting of ionizable materials including zinc, copper and silver.

12. The device of claim 10 further comprising an indicator signal for indicating activation of the electric field and correct delivery of a selected dose and dose rate.

13. The device of claim 10 wherein the device treats maladies selected from the group consisting of Herpes-type outbreaks, warts, acne, cold sores, and germicidal on dermatological infections.

14. The device of claim 10 further comprising circuitry for controlling the delivery rate of the metal ions, dose of the metal ions, waveform, and voltage.

15. The device of claim 10 further comprising a power source positioned within the bandage and a control system positioned within the bandage which automatically controls and modulates the electric field.

16. The device of claim 15 wherein the control system includes a controllable DC-to-DC converter to generate the required voltages and waveforms from a single cell battery to operate the device.

17. The device of claim 10 wherein the electric field is a bipolar field at low frequencies for maintaining a surface only distribution of the metal ions.

18. A method of infusing an antimicrobial metal ion into tissue of a body, the method comprising:

providing at least an antimicrobial metal ion source;

providing a contact surface;

contacting the tissue with metal ion source and the contact surface;

ionizing the antimicrobial metal ion source; and infusing the antimicrobial metal ions into the tissue applying an adhesive to the device to form a bandage strip and releasably securing the bandage strip to the tissue such that the antimicrobial metal ion source is in direct contact therewith.

19. The method of claim 18 further comprising providing an embedded microcontroller attached to the bandage strip and supporting circuitry for automatically controlling the delivery rate of the metal ions, dose of the metal ions, waveform, and voltage.

20. A portable hand-held device for treating an illness or infection of tissue of a body at a selected dose and dose rate of metal ions, the device comprising:

a housing with a visual indicator light thereon;

a metal ion source mounted on the housing which is directly contactable with the tissue;

a conducting surface mounted on the housing which is contactable with the user;

an automatically controlled and modulated field electrically connected to the metal ion source and the conducting surface automatically activated upon the metal ion source contacting the tissue and the conducting surface contacting the user;

wherein an electric field is created between the metal ion source and the conducting surface through the body such that the electric field causes the metal ion source to be ionized and perfuse metal ions into the tissue and activate the indicator light only upon determining that the selected dose and dose rate of metal ions is correct.

21. The device of claim 20 further comprising a microcontroller which controls the electric field between the metal ion source and conducting surface and a circuit board which connects the metal ion source to the conducting surface and microcontroller without the use of wires.

* * * * *